United States Patent [19]
Fricke et al.

[11] Patent Number: 4,877,038
[45] Date of Patent: Oct. 31, 1989

[54] HAND AND ARM RESTRAINT

[76] Inventors: Eberhard Fricke; Marie S. Fricke, both of 7021 Kittyhawk Ave., Los Angeles, Calif. 90045

[21] Appl. No.: 239,927

[22] Filed: Sep. 2, 1988

[51] Int. Cl.⁴ .............................................. A61F 13/00
[52] U.S. Cl. ..................................... 128/869; 128/876
[58] Field of Search ............... 128/869, 870, 871, 872, 128/873, 874, 875, 876, 94; 5/424, 485, 494

[56] References Cited

U.S. PATENT DOCUMENTS

| | | | |
|---|---|---|---|
| 438,639 | 10/1890 | Rapelye | 128/872 |
| 906,551 | 12/1908 | Newman | 5/494 |
| 1,061,259 | 5/1913 | Blofield | 5/494 |
| 1,621,323 | 3/1927 | Horn | 128/94 |
| 2,535,936 | 12/1950 | Langley | 128/873 |
| 2,560,243 | 7/1951 | Peterson | 128/94 |
| 2,586,961 | 2/1952 | Klein | 128/873 |
| 2,693,177 | 11/1954 | Barstow | 128/874 |
| 2,927,581 | 3/1960 | Queen | 128/873 |
| 3,060,462 | 10/1962 | Miller | 5/494 |
| 3,093,132 | 6/1963 | Bailey | 128/873 |
| 3,547,079 | 12/1970 | Bassett | 128/873 |
| 3,559,640 | 2/1971 | Beckett | 128/94 |
| 4,688,282 | 8/1987 | Jeffries | 5/494 |

FOREIGN PATENT DOCUMENTS 275138 11/1965 Australia .

Primary Examiner—Robert A. Hafer
Assistant Examiner—Michael Brown
Attorney, Agent, or Firm—Ashen Golant Martin & Seldon

[57] ABSTRACT

A hand and arm restraint (10) is provided for use with victims for Alzheimer's disease and other non-violent patients (13). The restraint has a pouch member (12) which is large enough to receive the hands, lower arms and at least a portion of the upper arms of the patient. The pouch member includes arm-receiving openings (26, 28), the size of which may be adjusted by adjusting ties (26', 28') in conjunction with a ring member 30 at the top corners (18, 20) of the pouch. Adjusting straps (34, 36) at each corner permit securing the pouch member to a bed frame and to adjust the location of the pouch member to enable the patient to comfortably fold his/her arms. The pouch member, which advantageously has an open weave material to permit visual inspection of the hands and arms of the patient by a caretaker, includes a zipper 32 along its bottom edge 16 to permit the caretaker to gain access to the hands and arms of the patient in order to check pulse, bathe the hands and arms, and perform other caretaking functions. The restraint avoids the chaffing and other irritation of the wrists of the patient, found on prior art restraints, while permitting the patient to clasp the hands and arms together for psychological comfort. The restraint further allows free blood flow, thereby eliminating hand swelling which occurs with prior art restraints and causes serious side effects.

10 Claims, 2 Drawing Sheets

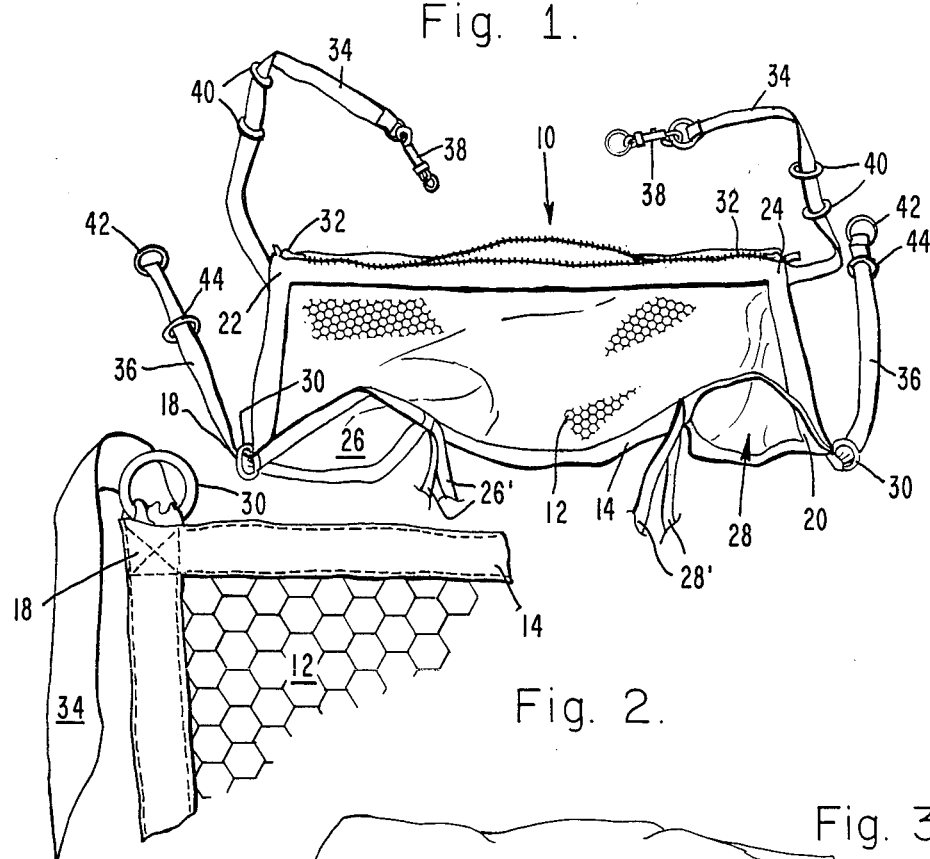
Fig. 1.
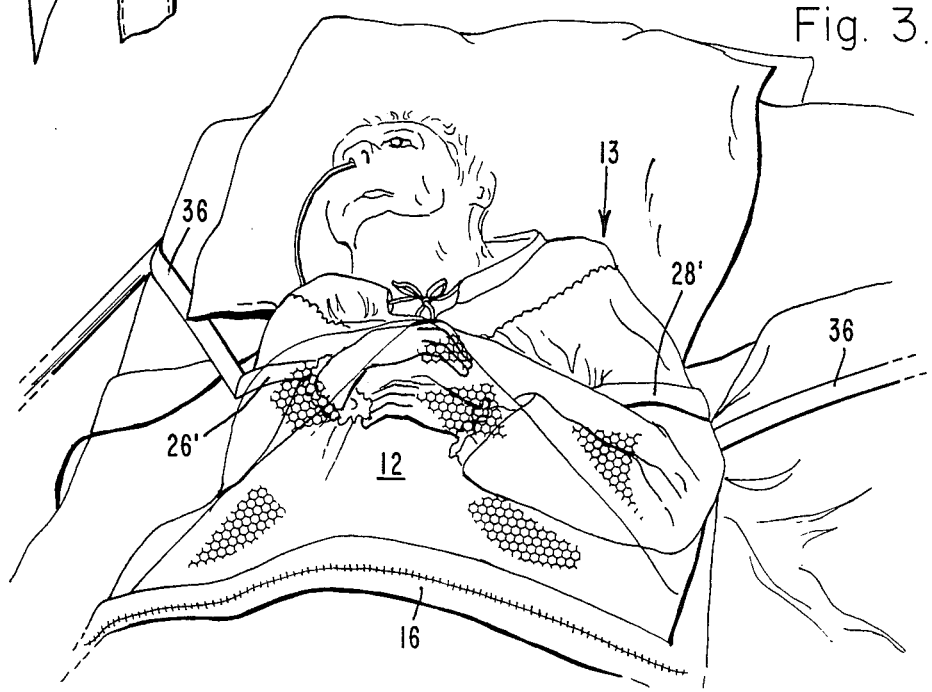
Fig. 2.
Fig. 3.

HAND AND ARM RESTRAINT

TECHNICAL FIELD

The present application relates to restraint systems, and, more particularly, to a hand and arm restraint for non-violent patients.

BACKGROUND ART

Victims of Alzheimer's disease and other non-violent patients often need to be restrained to a bed or other recumbent means for their own safety. For example, bed-ridden patients must be restrained from removing catheters or from wandering off.

There are many restraint systems available to restrain these non-violet patients to the bed, but most restraint systems are designed to restrain violent patients, and are strong and unyielding.

Some restraint systems have been adapted to nonviolent patients; and example includes wrist bands lined with fleece. These wrist restraints are tied to the sides of the bed, and force the wrists and hands to be separated, maintained along the sides of the patient. Many nonviolent patients struggle against such restraints, typically seeking to find comfort in clasping their hands together. In such struggles, even with fleece-lined restraints, the patients suffer from chaffed wrists and sores, as well as hand swelling from reducedd blood circulation. Further, they suffer the psychological eprivation of being unable to simply clasp their hands together.

With the noticeable increase in numbers of victims suffering from Alzheimer's disease and other debilitating diseases requiring passive restraint, a new apaproach to restraints is needed, one which will provide the necessary restraining action without physical chaffing of the victim, yet while permitting the victim to enjoy the psychological comfort of being able to clasp the hands together.

DISCLOSURE OF INVENTION

In accordance with the invention, a hand and arm restraint is provided, which comprises a pouch member large enough to at least receive the hands, lower arms, and at least a portion of the upper arms of the patient. The pouch member has a top edge and a bottom edge and four corners. Two arm-receiving openings are disposed along the top edge, near the corners thereof. Means for gaining access to the interior of the pouch is provided along the bottom edge. Straps are provided at each corner for securing the pouch member, such as by attachment to suitable locations on a bed frame or other recumbent means. Ties are advantageously associated with the arm-receiving openings for adjusting the extent of the opening and to further secure the restraint on the patient.

The configuration of pouch member permits the patient to clasp his or her hands together or otherwise hold the arms together, thereby providing psychological comfort. The access means along the bottom of the pouch member may comprise a zipper along the entire length thereof, and permits a caretaker to bathe the hands and arms, take pulse reading, or simply touch the hands and/or arms of the patient for further psychological comfort.

Most importantly, use of the restraint of the invention prevents bed-ridden from removing catheters, while allowing hand and arm movement between the waist and arm-pit level. Further, hand swelling due to reduced circulation caused by prior art restraints is eliminated by the restraint.

BRIEF DESCRIPTION OF THE DRAWINGS

FIG. 1 is a view of the restraint of the invention from the patient's point of view;

FIG. 2 is a detailed view of one top corner, depicting an open weave mesh which is preferably employed asa the material comprising the main part of the restraint;

FIG. 3 is a perspective view, showing the restraint as applied to a bed-ridden patient;

BEST MODES FOR CARRYING OUT THE INVENTION

Figure 4:
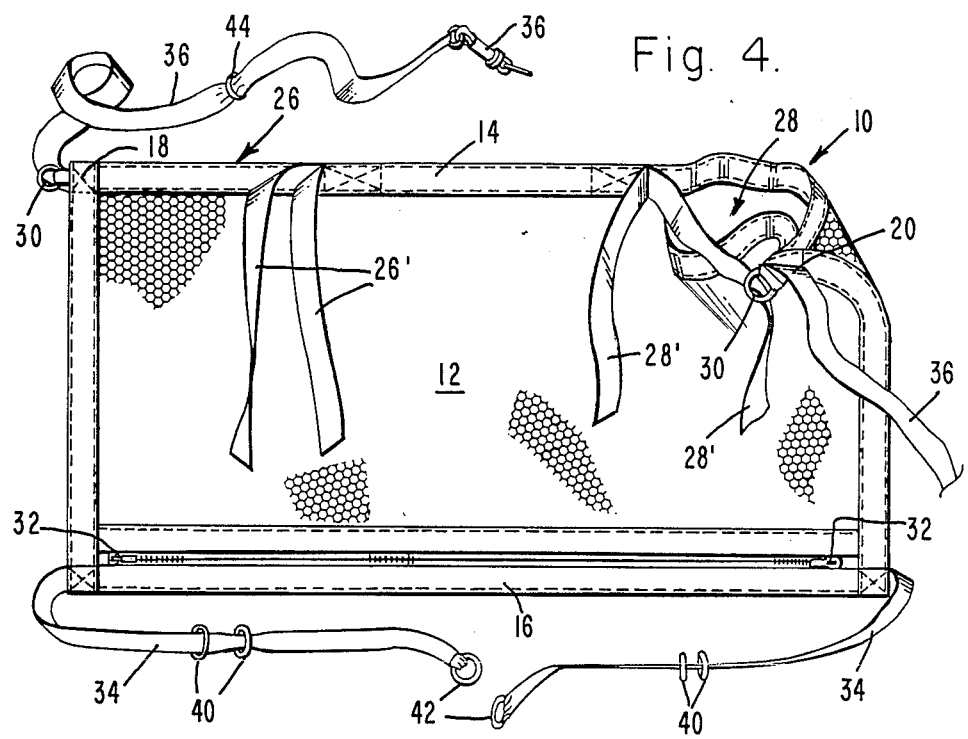
FIG. 4 is a plan view of the restraint, depicting use of ties to adjust the diameter of one arm-engaging opening.

Referring now to the drawings, wherein like numerals depict like elements of reference, FIG. 1 depicts the hand and arm restraint of the invention. The restraint 10 comprises a pouch member 12 large enough to at least receive the hands, lower arams, and at least a portion of the upper arms of a patient 13, typically a non-violent patient such as one suffering from Alzheimer's disease.

The pouch member 10 has a top edge 14 and a bottom edge 16 and four corners 18, 20, 22, 24. Two arm receiving openings 26, 28 are disposed along the top edge 14, near the corners 18, 20 thereof. Each opening is preferably provided means for adjusting the opening thereof, to prevent the patient 13 from removing his/her arms. Such means may comprise, for example, a pair of tie straps 26', 28', disposed inwardly from the corner 18, 20, and associated with a ring member 30 disposed at each corner 18, 20. FIG. 4 depicts the initial stages of tying the straps 26', 28' to adjust the opening; one strap is shown through a ring member 30. The free ends of the straps may be tied together to form a non-slippable knot. Use of the ring member 30 in conjunction with one strap is seen to reduce the size of the opening.

Figure 5:
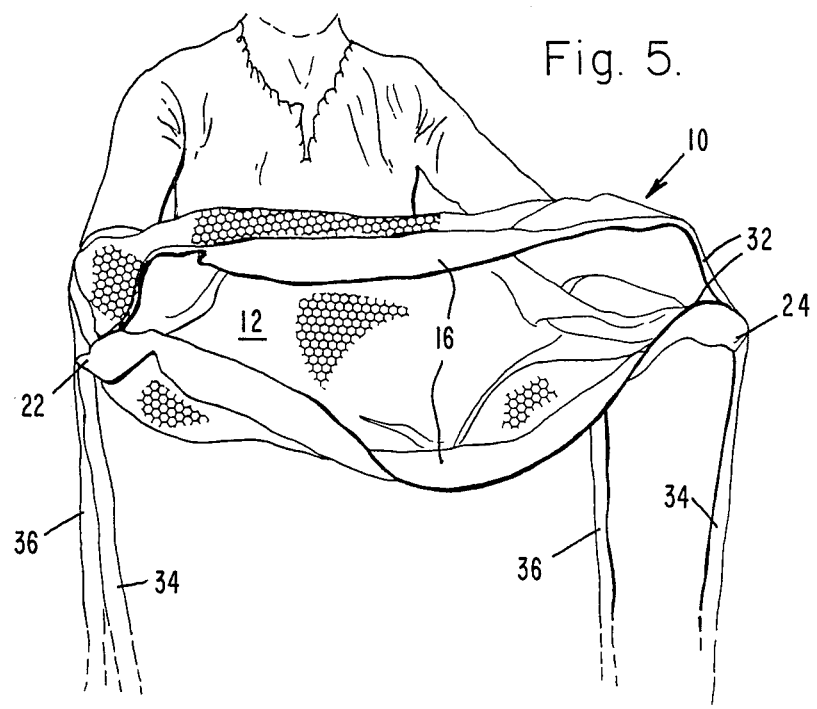
FIG. 5 is a view from the opened bottom of the restraint, depicting access by a caretaker.

Means for gaining access to the interior of the pouch 12 is provided along the botom edge 16 thereof. Such means may comprise, for example, a two-way zipper 32, as best seen in FIG. 1. FIG. 5 depicts the bottom of the pouch completely open; in such a configuration, the caretaker may gain access to the patient's hands and arms for cleaning purposes, for taking pulse, or for other necessary caretaking functions.

At each corner 18, 20, 22, 24 is a strap means for securing the pouch member 12 to suitable locations on a bed frame or other recumbent means. FIGS. 1 and 4 depict two types of straps 34, 36 suitably employed in the practice of the invention. Straps 34 terminate in a buckle 38 which is readily attachable to an eyebolt (not shown) on a bed frame. A pair of ring members 40 may be employed to adjust the length of the strap 34. Other adjusting means may alternately be employed.

Straps 36 terminate in a ring member 42, which attaches to a buckle, such as a buckle 38 already secured to the bed frame. Ring member 42 would alternately allow buckle 38 to be attached on ring 42 and wrapped around vertically-disposed bed rails, securing to adjusting ring members 44. A pair of ring members 44 may be employed to adjust the length of the strap 36, as with strap 34. Again, alternate adjusting means may be used.

The particular attaching means (e.g., buckle 38 and ring 42) may be interchangeably employed on either securing straps 34 or 36, the particular attaching means being dictated by the type of securement on the bed frame. In this connection, other well-known attaching means may alternately be employed as appropriate in the practice of the invention.

Both straps 34 and 36 are of a sufficient length to secure the pouch member 12 to the bed frame. For exemplary purposes only, the pouch member 12 my smesaure 29-1/2 inches long and 15-1/2 inches wide. Tie straps 26, 28 may be about 12 inches long and 1 inch wide. Securing strap means 34 and 36 may be about 26 to 28 inches long and 1 inch wide.

In construction, the pouch member 12 may comprise an open weave nylon material, having a mesh size of 5/16 inch, although other mesh sizes and other materials of the requisite strength may be used, it being only sufficient to permit free flow of air and visual access of the hands and arms of the patient. The open weave is attached along each edge by a sturdy nylon strap material, advantageously about 1 inch wide, double-stitched as appropriate.

In use, the arms of the patient 13 are inserted through the openings 26, 28, and the openings are adjusted to fit the arms of the patient by inserting one adjusting tie member 26', 28' of each opening through ring member 30 and tying the members together tight enough to prvent removal of an arm by the patient, but not so tight as to impede circulation in the arm of the patient. The securing straps 34, 36 are suitably attached to securing points on the bed frame and are adjusted in length so that the patient's hands and arms lie across the abdomen, as showon in FIG. 3.

It will be seen that the configuration of the pouch member 12 permits the patient 13 to clasp his or her hands together or otherwise hold the arms together, thereby providing psychological comfort. The access means along the bottom of the pouch member may comprise a zipper 32, advantageously a two-way zipper, along the entire length 16 thereof, and permits a care-taker to bathe the hands and arms, take pulse reading, or simply touch the hands and/or arms of the patient for further psychological comfort.

It will be appreciated that use of the restraint of the invention prevents bed-ridden from removing catheters, while allowing hand and arm movement between the waist and armpit level. Further, hand swelling due to reduced circulation caused by prior art restraints is eliminated by the restraint.

INDUSTRIAL APPLICABILITY

The hand and arm restraint is expected to find use in hospitals, nursing homes, private homes, etc. to enable non-violent patients, such as victims of Alzheimer's disease, to be restrained in a manner to avoid chaffing of hands and arms, to permit free blood circulation through the hands, and to permit the patient to attain the psychological satisfaction of being able to clasp the hands and arms together.

Thus, there has been disclosed a hand and arm restraint for non-violent patients. It will be readily seen by those of ordinary skill in this art that various changes and modifications of an obvious nature may be made without departing from the spirit and scope of the invention, and all such changes and modifications are considered to fall with the ambit of the invention, as defined by the appended claims.

What is claimed is:

1. A hand and arm restraint comprising a pouch member of a size large enough to receive the hands, lower arms, and at least a portion of the upper arms of a patient, said pouch member having a top edge, a bottom edge, and four corners, two corners being associated with said top edge and two corners being associated with said bottom edge, with two arm-receiving openings disposed along said top edge and separated by a distance similar to that of said arms of said patient, each arm-receiving opening provided with a pair of ties for adjusting the extent of said opening so as to prevent removal of an arm therefrom, and zipper means disposed along said bottom edge for gaining access by a care-taker to the interior of said pouch member.

2. The restraint of claim 1 wherein said pouch member comprises an open-weave material of a mesh size to permit free flow of air and visual access of said hands and arms of said patient.

3. The restraint of claim 1 further comprising means for securing said pouch to a patient-supporting recumbent means.

4. The restraint of claim 3 wherein said securing means comprises a plurality of straps for attaching to suitable anchor points on said recumbent means.

5. The restraint of claim 4 wherein each strap is attached at one of said corners of said pouch, at least two of said straps suitably provided with adjustable means for adjusting the length thereof.

6. A hand and arm restraint for non-violent patients comprising a pouch member of a size large enough to receive the hands, lower arms, and at least a portion of the upper arms of a patient, said pouch member having
   (a) a top edge, a bottom edge, and four corners, two corners being associated with said top edge and two corners being associated with said bottom edge;
   (b) two arm-receiving openings disposed along said top edge and separated by a distance similar to that of said arms of said patient, wherein each arm-receiving opening is provided with a pair of ties for adjusting the extent of said opening so as to prevent removal of an arm therefrom;
   (c) zipper means disposed along said bottom edge for gaining access by a care-taker to the interior of said pouch member; and
   (d) means for securing said pouch to a patientsupporting recumbent means.

7. The restraint of claim 6 wherein said pouch member comprises an open-weave material of a mesh size to permit free flow of air and visual access of said hands and arms of said patient.

8. The restraint of claim 6 wherein said securing means comprises a plurality of straps, each strap attached to, one of said corners of said pouch, at least two of which straps are suitably provided with adjustable means for adjusting the length thereof, for attaching to suitable anchor points on said recumbent means.

9. The restraint of claim 8 wherein said securing means comprises four straps, one strap attached to each corner of said pouch, each strap adjustable to different lengths.

10. A hand and arm restraint for non-violent patients comprising a pouch member of a size large enough to receive the hands, lower arms, and at least a portion of the upper arms of a patient, said pouch member comprising an open weave material of a mesh size to permit free flow of air and visual access of said hands and arms of said patient and having (a) a top edge, a bottom edge, and four corners, two corners being associated with said top edge and two corners being associated with said bottom edge;

(b) two arm-receiving openings disposed along said top edge and separated by a distance similar to that of said top arms of said patient, wherein each arm-receiving opening is provided with a pair of ties for adjusting the extent of said opening so asa to prevent removal of an arm therefrom;

(c) a zipper disposed along said bottom edge for gaining access by a care-taker to the interior of said pouch member; and (d) four straps for securing said pouch to a bed, each strap attached to one of said corners of said pouch, each strap suitably provided with adjustable means for adjusting the length thereof and provided with attachment means for attaching said strap to suitable anchor points on said bed.

* * * * *